(12) United States Patent
Kobayashi et al.

(10) Patent No.: US 8,278,119 B2
(45) Date of Patent: Oct. 2, 2012

(54) DETECTION METHOD AND DETECTION REAGENT FOR AUTOIMMUNE PANCREATITIS OR FULMINANT TYPE-1 DIABETES

(75) Inventors: Tetsuro Kobayashi, Yamanashi (JP); Toyoshi Endo, Yamanashi (JP); Atsushi Sakuraoka, Tokyo (JP)

(73) Assignees: University of Yamanashi, Kofu-shi, Yamanashi (JP); Cosmic Corporation, Bunkyo-ku, Tokyo (JP)

( * ) Notice: Subject to any disclaimer, the term of this patent is extended or adjusted under 35 U.S.C. 154(b) by 280 days.

(21) Appl. No.: 12/598,416

(22) PCT Filed: May 2, 2008

(86) PCT No.: PCT/JP2008/058413
§ 371 (c)(1), (2), (4) Date: Oct. 30, 2009

(87) PCT Pub. No.: WO2008/136510
PCT Pub. Date: Nov. 13, 2008

(65) Prior Publication Data
US 2010/0129832 A1 May 27, 2010

(30) Foreign Application Priority Data
May 2, 2007 (JP) .................. 2007-121461

(51) Int. Cl.
- C07K 14/435 (2006.01)
- C07K 16/18 (2006.01)
- C07K 16/40 (2006.01)
- C12Q 1/40 (2006.01)
- G01N 33/543 (2006.01)
- G01N 33/564 (2006.01)
- G01N 33/573 (2006.01)

(52) U.S. Cl. ......... 436/506; 435/7.1; 435/7.4; 435/7.92; 435/7.95; 435/22; 435/69.3; 435/975; 436/507; 436/513; 436/518; 436/531; 436/543; 436/811; 530/350; 530/391.3; 530/403; 530/806; 530/810; 530/815; 530/845

(58) Field of Classification Search .............. 435/7.1, 435/7.4, 7.92, 7.95, 69.3, 975, 22; 436/506, 436/507, 513, 518, 531, 543, 811; 530/350, 530/391.3, 403, 806, 810, 815, 845
See application file for complete search history.

(56) References Cited

U.S. PATENT DOCUMENTS
2003/0186345 A1* 10/2003 Hortin ........................... 435/23
(Continued)

FOREIGN PATENT DOCUMENTS
EP 1 775 590 4/2007
(Continued)

OTHER PUBLICATIONS

Hortin et al., 1994. Detection of autoantibodies to amylase by ELISA: comparison of detection of macroamylase and free autoantibody. Clinical Chemistry 40: 2254-2259.*

(Continued)

*Primary Examiner* — Gail R Gabel
*Assistant Examiner* — James L Grun
(74) *Attorney, Agent, or Firm* — Knobbe, Martens, Olson & Bear, LLP

(57) ABSTRACT

By detecting an antibody which immunologically reacts with amylase α2-A in a sample, AIP or FT1DM is examined or the possibility of developing FT1DM is determined. For instance, detection of this antibody is carried out by an immunological method using an antigen which immunologically reacts with this antibody. The antigen is preferably a partial fragment containing the amino acid sequence of amino acid numbers 299 to 511 of human amylase α2-A (SEQ ID NO: 1).

12 Claims, 3 Drawing Sheets

U.S. PATENT DOCUMENTS

2008/0166741 A1* 7/2008 Tseng et al. .................. 435/7.92

FOREIGN PATENT DOCUMENTS

JP    2005-253434    9/2005

OTHER PUBLICATIONS

Barera et al., 2001. Macroamylasemia attributable to gluten-related amylase autoantibodies: a case report. Pediatrics 107: e93.1-e93.4.*

Saebø, et al. "Acute and Chronic Pancreatic Disease Associated with *Yersinia enterocolitica* Infection; A Norwegian 10-year Follow-up Study of 458 Hospitalized Patients," *Journal of Internal Medicine*, vol. 231, No. 5, pp. 537-541, 1992.

Sato, et al. "Suspected Fulminant Type 1 Diabetes with Autoantibodies to the Exocrine Pancreas and Nonspecific Abnormal Humoral Immunity," *Journal of the Japan Diabetes Society*, vol. 48, No. 3, p. 181, 2005.

Supplementary European Search Report dated Apr. 26, 2010 and issued to European application No. EP 08 75 2318.

Davidson, et al. An Experimental Model of Autoimmune Pancreatitis in the Rat, *American Journal of Pathology*, vol. 166, No. 3, pp. 729-736, 2005.

International Search Report issued to a counterpart international application dated Jun. 10, 2008.

* cited by examiner

SEQUENCE LISTING

```
<160> NUMBER OF SEQ ID NOS: 3

<210> SEQ ID NO 1
<211> LENGTH: 511
<212> TYPE: PRT
<213> ORGANISM: Homo sapiens

<400> SEQUENCE: 1

Met Lys Phe Phe Leu Leu Leu Phe Thr Ile Gly Phe Cys Trp Ala Gln
1               5                   10                  15

Tyr Ser Pro Asn Thr Gln Gln Gly Arg Thr Ser Ile Val His Leu Phe
            20                  25                  30

Glu Trp Arg Trp Val Asp Ile Ala Leu Glu Cys Glu Arg Tyr Leu Ala
        35                  40                  45

Pro Lys Gly Phe Gly Gly Val Gln Val Ser Pro Pro Asn Glu Asn Val
    50                  55                  60

Ala Ile Tyr Asn Pro Phe Arg Pro Trp Trp Glu Arg Tyr Gln Pro Val
65                  70                  75                  80

Ser Tyr Lys Leu Cys Thr Arg Ser Gly Asn Glu Asp Glu Phe Arg Asn
            85                  90                  95

Met Val Thr Arg Cys Asn Asn Val Gly Val Arg Ile Tyr Val Asp Ala
            100                 105                 110

Val Ile Asn His Met Cys Gly Asn Ala Val Ser Ala Gly Thr Ser Ser
            115                 120                 125

Thr Cys Gly Ser Tyr Phe Asn Pro Gly Ser Arg Asp Phe Pro Ala Val
    130                 135                 140

Pro Tyr Ser Gly Trp Asp Phe Asn Asp Gly Lys Cys Lys Thr Gly Ser
145                 150                 155                 160

Gly Asp Ile Glu Asn Tyr Asn Asp Ala Thr Gln Val Arg Asp Cys Arg
                165                 170                 175

Leu Thr Gly Leu Leu Asp Leu Ala Leu Glu Lys Asp Tyr Val Arg Ser
            180                 185                 190

Lys Ile Ala Glu Tyr Met Asn His Leu Ile Asp Ile Gly Val Ala Gly
        195                 200                 205

Phe Arg Leu Asp Ala Ser Lys His Met Trp Pro Gly Asp Ile Lys Ala
    210                 215                 220
```

```
Ile Leu Asp Lys Leu His Asn Leu Asn Ser Asn Trp Phe Pro Ala Gly
225                 230                 235                 240

Ser Lys Pro Phe Ile Tyr Gln Glu Val Ile Asp Leu Gly Gly Glu Pro
                245                 250                 255

Ile Lys Ser Ser Asp Tyr Phe Gly Asn Gly Arg Val Thr Glu Phe Lys
            260                 265                 270

Tyr Gly Ala Lys Leu Gly Thr Val Ile Arg Lys Trp Asn Gly Glu Lys
        275                 280                 285

Met Ser Tyr Leu Lys Asn Trp Gly Glu Gly Trp Gly Phe Val Pro Ser
290                 295                 300

Asp Arg Ala Leu Val Phe Val Asp Asn His Asp Asn Gln Arg Gly His
305                 310                 315                 320

Gly Ala Gly Gly Ala Ser Ile Leu Thr Phe Trp Asp Ala Arg Leu Tyr
                325                 330                 335

Lys Met Ala Val Gly Phe Met Leu Ala His Pro Tyr Gly Phe Thr Arg
                340                 345                 350

Val Met Ser Ser Tyr Arg Trp Pro Arg Gln Phe Gln Asn Gly Asn Asp
            355                 360                 365

Val Asn Asp Trp Val Gly Pro Pro Asn Asn Asn Gly Val Ile Lys Glu
        370                 375                 380

Val Thr Ile Asn Pro Asp Thr Thr Cys Gly Asn Asp Trp Val Cys Glu
385                 390                 395                 400

His Arg Trp Arg Gln Ile Arg Asn Met Val Ile Phe Arg Asn Val Val
                405                 410                 415

Asp Gly Gln Pro Phe Thr Asn Trp Tyr Asp Asn Gly Ser Asn Gln Val
                420                 425                 430

Ala Phe Gly Arg Gly Asn Arg Gly Phe Ile Val Phe Asn Asn Asp Asp
            435                 440                 445

Trp Ser Phe Ser Leu Thr Leu Gln Thr Gly Leu Pro Ala Gly Thr Tyr
        450                 455                 460

Cys Asp Val Ile Ser Gly Asp Lys Ile Asn Gly Asn Cys Thr Gly Ile
465                 470                 475                 480

Lys Ile Tyr Val Ser Asp Asp Gly Lys Ala His Phe Ser Ile Ser Asn
                485                 490                 495

Ser Ala Glu Asp Pro Phe Ile Ala Ile His Ala Glu Ser Lys Leu
                500                 505                 510

<210> SEQ ID NO 2
<211> LENGTH: 35
<212> TYPE: DNA
<213> ORGANISM: Artificial Sequence
<220> FEATURE:
<223> OTHER INFORMATION: primer

<400> SEQUENCE: 2
atggggatcc ttggggtttc gtaccttctg acaga                              35

<210> SEQ ID NO 3
<211> LENGTH: 35
<212> TYPE: DNA
<213> ORGANISM: Artificial Sequence
<220> FEATURE:
<223> OTHER INFORMATION: primer

<400> SEQUENCE: 3
cttcgaattc ccaatttaga ttcagcatga attgc                              35
```

DETECTION METHOD AND DETECTION REAGENT FOR AUTOIMMUNE PANCREATITIS OR FULMINANT TYPE-1 DIABETES

CROSS-REFERENCE TO RELATED APPLICATIONS

This application is the U.S. National Phase under 35 U.S.C. §371 of International Application PCT/JP2008/058413, filed May 2, 2008, which was published in a non-English language, which claims priority to JP Application No. 2007-121461, filed May 2, 2007.

TECHNICAL FIELD

The present invention relates to a method for examination of autoimmune pancreatitis (AIP) and fulminant type 1 diabetes mellitus (FT1DM) as well as a reagent for examination thereof.

BACKGROUND ART

Currently, diagnoses of AIP are carried out based on "Autoimmune pancreatitis diagnostic criteria" released by Japan Pancreas Society in 2002. According to the criteria, a sufficient condition for the diagnosis is that any one of hyper-gammaglobulinemia, hyperimmunoglobulinemia G, and autoantibodies, all of which are items in a blood test, is observed. Further, it has been reported that in hyperimmunoglobulinemia G, the IgG4 subclass specifically increased as the autoantibodies, anti-nuclear antibodies and rheumatoid factors could be positive.

Hence, in a blood test for the present disease, these items namely gamma globulins, IgGs, IgG4, anti-nuclear antibodies (SS-A antibody and SS-B antibody) and rheumatoid factors, must be measured and thus the cost is very high, which is problematic. In addition, these test items are also increased or positive in other diseases so that the diagnostic specificity based upon measurement of the above items is poor. Further, even when the present disease is diagnosed in accordance with the above-described criteria, it is very difficult to distinguish from pancreatic cancer, and an unnecessary operation may be performed. And thus, a method for reliably distinguishing both diseases is desirable.

Each investigator has been searching for an autoantibody specific to AIP and thus far found activities of anti-blood lactoferrin (LF) antibody and anti-carbonic anhydrase II (CAII) antibody. Yet, the positive ratio of the antibodies in AIP is 73% and 53.8%, respectively, which lacks clinical sensitivity. Reliability and reproducibility of the method are poor. Therefore, these antibodies are inappropriate for diagnosis and differential diagnosis (Non-patent Literature References 1 and 2).

Furthermore, although monitoring the progress of an AIP treatment by a blood test is necessary for determining dosage and timing of administration, due to the same reasons as described above, the high testing cost is problematic.

Currently, diagnoses for FT1DM are carried out based on "Fulminant type 1 diabetes mellitus diagnostic criteria" presented by the research committee on fulminant diabetes mellitus of The Japan Diabetes Society in 2004. According to that, as a laboratory sample test, HbA1C, blood sugar level and C-peptide in urine or blood are measured. Further, as reference observations, it should be checked if autoantibodies such as GAD antibody and IA-2 antibody are negative and if blood pancreatic exocrine enzyme is increased.

Accordingly, with regard also to the present disease, a large number of items need to be tested, the cost for the diagnosis is high, and the test is non-specific, which is problematic.

Additionally, in many cases, the present disease develops into ketoacidosis within several days after the onset of the symptoms of hyperglycemia. Thus, without reliable diagnosis and prompt initiation of the treatment, the patient faces a life-threatening situation. Also, the disease often develops during pregnancy, which causes fetal death in most cases. Accordingly, it is desirable that the above-described test items be measured upon the onset of general diabetes mellitus to distinguish FT1DM from type 1 diabetes mellitus and type 2 diabetes mellitus. Yet, because no test marker for a good diagnosis to exclude FT1DM is available and the number of the test items is large, in reality, the differential diagnosis is not carried out.

Non-patent Literature 1: *N. Engl. J. Med.* 2001, 344:732-8
Non-patent Literature 2: *J. Gastroenterol.* 2001, 36:293-302

DISCLOSURE OF THE INVENTION

The present invention has been made in view of such drawbacks in the prior art and an object of the invention is to provide a method for examination of autoimmune pancreatitis (AIP) and fulminant type 1 diabetes mellitus (FT1DM) and a testing reagent therefor.

The present inventors have discovered the presence of an antibody against amylase α2-A in the serum of patients with AIP, patients with FT1DM as well as those who have a high possibility of developing FT1DM, thereby completing the present invention.

That is, the present invention provides the followings:

(1) A method for examination of autoimmune pancreatitis, which method comprises detecting an antibody which immunologically reacts with amylase α2-A in a sample, thereby examining autoimmune pancreatitis, (2) A method for examination of fulminant type 1 diabetes, which method comprises detecting an antibody which immunologically reacts with amylase α2-A in a sample, thereby examining fulminant type 1 diabetes, (3) A method for examination of the possibility of developing fulminant type 1 diabetes, which method comprises detecting an antibody which immunologically reacts with amylase α2-A in a sample, thereby determining the possibility of developing fulminant type 1 diabetes.

In the above-described methods for examination (1) to (3), the above-described antibody is preferably detected by using an antigen which immunologically reacts with the above-described antibody. The antigen is preferably a partial fragment comprising the amino acid sequence of amino acid numbers 299 to 511 of human amylase α2-A (SEQ ID NO: 1).

Also, the present invention provides a reagent for examination used in the above-described methods for examination (1) to (3), which reagent comprises an antigen which immunologically reacts with an antibody which immunologically reacts with amylase α2-A.

The antigen is preferably a partial fragment comprising the amino acid sequence of amino acid numbers 299 to 511 of human amylase α2-A (SEQ ID NO: 1).

The diagnosis of autoimmune pancreatitis by measuring the anti-amylase antibody is specific. Hence, the cost is reduced by examining only one item and unnecessary operations or drug administration are decreased because the differential diagnosis from pancreatic cancer is assured and treatment follow-ups are possible, thereby attaining significant reduction of the healthcare cost.

Differentiation between fulminant type 1 diabetes mellitus and acute type 1 and type 2 diabetes mellitus, as described in the prior art section, is not actually carried out because no specific maker is available and the number of the items to be examined for the diagnosis to exclude fulminant type 1 diabetes mellitus is large. Yet, with the measurement according to the present invention, definitive diagnosis and differential diagnosis can be carried out by measuring only one item. Also, by applying the present measurement method to a simple measurement method such as an immunochromatography method, diagnosis of type 1 diabetes mellitus can be further quickly carried out on site. In this way, it is possible to make an early diagnosis and to save a patient (in addition, a fetus of the patient) whose life is not saved by conventional treatments. At the same time, the method can greatly contribute to reduction of the cost for laboratory testing and reduction of the healthcare cost due to the advancement of the disease. Also, the test for the possibility of developing fulminant type 1 diabetes mellitus greatly contributes to reduction of the healthcare cost as well.

BEST MODE FOR CARRYING OUT THE INVENTION

Figure 1:
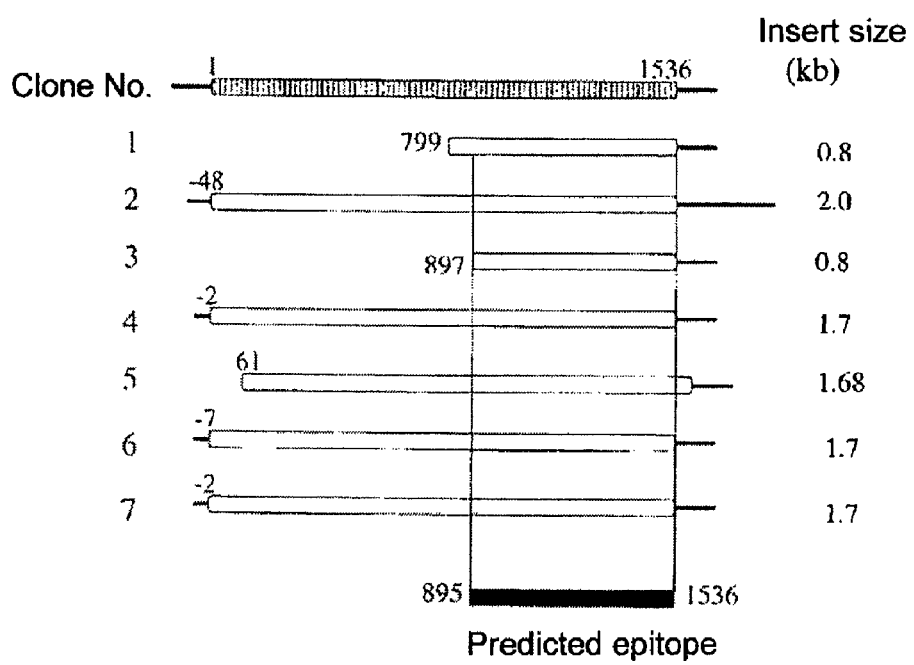
FIG. 1 shows cDNA clones of human amylase α-2 obtained in Reference Example 1, which clones are obtained from the human pancreas cDNA library. "A" in the start codon ATG was designated as 1.

The mode for carrying out the present invention will now be described below. First, the method for examination according to the present invention will be described.

The method for examination according to the present invention is characterized by detecting an antibody which immunologically reacts with amylase α2-A (hereinafter also referred to as "anti-AMY-2A antibody" in a sample, thereby examining autoimmune pancreatitis (AIP) and fulminant type 1 diabetes mellitus (FT1DM) or determining the possibility of developing FT1DM.

A method for detection is not restricted as long as it can detect the anti-AMY-2A antibody. Usually, an example thereof includes an immunological method using an antigen or antibody which immunologically reacts with the anti-AMY-2A antibody. Since antigens are more readily prepared than antibodies, it is preferred to use an immunological method using the antigen which immunologically reacts with the anti-AMY-2A antibody. An example of the immunological method includes ELISA which is widely used in general.

As long as the antigen immunologically reacts with anti-AMY-2A antibody present in a sample, any antigen can be employed. An amylase molecule purified from human or animals can be used. The amylase molecule may be prepared by a recombinant technique. For instance, a base sequence encoding human amylase α2-A is known (GenBank accession number M28443). Also, a partial fragment of the amylase molecule can be used as long as it immunologically reacts with the anti-AMY-2A antibody present in a sample.

From the viewpoint of stable supply of the antigen and its homogeneity as a protein molecule, the partial fragment of amylase is preferably used. When the partial fragment of amylase is used, molecules with homogeneity can be readily prepared and, as a result, reliability of the measurement improves.

An example of such a partial fragment includes a partial fragment containing the amino acid sequence of amino acid numbers 299 to 511 of human amylase α2-A (SEQ ID NO: 1). Also, even with a mutation in the amino acid sequence, a partial fragment corresponding to amino acid numbers 299 to 511 of SEQ ID NO: 1 can be used.

Although a sample subjected to measurement is usually the serum, as long as it does not contain a substance that interferes with a reaction in the reaction process, it is not restricted.

A condition for the detection can be the same condition as in a conventional immunological method. That is, conditions such as an addition order and amount of each reaction substance, reaction temperature, and reaction time may be the same as in a conventional immunological method. An example includes a method in which an antigen immobilized onto a solid phase, such as a tube or plate, is allowed to react with the serum and after removing unbound IgGs contained in the serum, an anti-IgG antibody labeled with an enzyme is bound to the antibody bound to the antigen to detect the anti-AMY-2A antibody by an enzyme reaction.

The amount of anti-AMY-2A antibody is usually calculated as a measured value of the label. Alternatively, the concentration can be determined based on a calibration curve which is prepared with a standard sample containing a known concentration of the anti-AMY-2A antibody.

Positive determination can be made by comparing with a value of a healthy normal subject. When the value of the sample is statistically significantly greater than that of the healthy normal subject simultaneously measured or previously measured (for instance, greater by 2SD or more, or statistically significantly greater based on a statistical test), the sample can be determined to be positive.

An increase in the anti-AMY-2A antibody measured by the method for examination according to the present invention is specific to AIP and FT1DM. Hence, by the method for examination according to the present invention, when AIP or FT1DM is suspected, measurement of only one item allows AIP or FT1DM to be specifically examined.

Also, without the onset of FT1DM, the possibility of developing FT1DM can be determined. In the case of being positive, it can be determined that the possibility of developing the disease is high.

Next, the reagent for examination according to the present invention will be described. The reagent for examination according to the present invention is a reagent for carrying out the method for examination according to the present invention, which reagent comprises the antigen which immunologically reacts with the anti AMY-2A antibody.

The antigen which immunologically reacts with the anti AMY-2A antibody is as described regarding the method for examination according to the present invention.

Further, the reagent for examination according to the present invention may comprise, as needed, reagents necessary for immunological measurement, for example, a positive control, buffer, or the like, and may be provided as a kit.

Each component of the reagent for examination according to the present invention may be in a solution state or in a dry state as exemplified by a freeze-dried product. In cases where the component is in a dry state, a buffer or the like to make it into a solution prior to use can be included in the reagent for examination according to the present invention. The amount and form of each component can be adjusted in accordance with conditions of the measurement method.

For instance, as for an ELISA kit, it can be a kit containing a solid phase plate onto which an antigen is immobilized, washing solution, sample diluting solution, solution with an enzyme-labeled anti-AMY-2A antibody, substrate solution, and reaction stop solution. In addition, a kit for an immunochromatography method can be a kit containing a reaction device and developing solution.

EXAMPLES

The present invention will be described by means of examples below. In the examples, all "%" are by weight unless otherwise noted.

Reference Example 1

Cloning of cDNA from Human Pancreas

Human pancreas cDNA library (λTriplEx2 human pancreas large insert cDNA library, BD Bioscience Clontech) and *E. coli* XL-1 competent cells (BD Bioscience Clontech) were used. Plaques on a plate were transferred to a nitrocellulose membrane previously immersed in 10 mM isopropyl-β-D-thiogalactsides (IPTG). The resulting membrane was washed with Tris buffered saline (TBST) containing 0.05% Tween 20 and blocked with Tris buffered saline containing 1% bovine serum albumin. The membrane was incubated overnight at 4° C. together with serum (diluted 500 fold with TBST) provided from a patient with chronic pancreatitis (AIP) (67 years old, male). Then, the membrane was washed with TBST four times and allowed to react with goat horseradish peroxidase-conjugated anti-human IgG (American Qualex, diluted 2,000 fold with TBST) at room temperature for 30 minutes. The membrane was washed with TBST four times and a positive reaction was detected with 3,3'-diaminobenzidine.

By the method described above, $2 \times 10^4$ plaques obtained by using the serum of the AIP patient were screened and ten positive clones were obtained.

A cDNA fragment of the positive clone was amplified by PCR using a sense primer 5'-ATGGGGATCCT-TGGGGTTTCGTACCTTCTGACAGA-3' (SEQ ID NO: 2) and an antisense primer 5'-CTTCGAATTCCCAATTTA-GATTCAGCATGAATTGC-3' (SEQ ID NO: 3). The PCR product was digested with BamHI and EcoRI and the resultant fragment was ligated to pTrcHisB (Invitrogen). By sequencing the inserted cDNA and homology search, seven out of ten clones had the same sequence as human AMY-2A. As a result of comparing with the sequence of human AMY-2A cloned by Wise et al. (*J. Mol. Biol. Med.* 2:307-322, 1984), as shown in FIG. 1, four out of seven clones contained the entire length of the coding sequence and the 5' terminus of the other three clones was respectively +61, +799, and +897 ("A" in ATG was assigned as 1). Other clones which were not amylase clones were housekeeping genes such as heat shock proteins and nuclear proteins.

Reference Example 2

ELISA for Detecting the Antibody Against Human Amylase α2-A (AMY-2A)

As shown in Reference Example 1, IgG of the AIP patient used for the screening recognized various lengths of the clones of AMY-2A. The region shared by these seven clones was thought to contain a common epitope of the patient's IgG (the predicted epitope in FIG. 1). Thus, human AMY-2A fragment from codon 299 to 512 (AMY-2A/299-512) with a histidine tag was prepared using *E. coli* BL21. Specifically, after sequencing, the plasmid was transfected into *E. coli* BL-21 (Novagen) and the recombinant protein was generated by induction with 1 mM IPTG and purified with a His Bond column chromatography.

In accordance with the ELISA described in *Diabetes Care* 24:1661-7, 2001, the prepared protein was coated on a plate to construct ELISA for detecting the anti-amylase antibody in the serum. Details are as follows: a microtiter plate (Coster 3590, Corning Inc.) was coated with 0.1 μg (50 μl) of recombinant human AMY-2A at 4° C. overnight. The plate was washed with phosphate-buffered saline (PBST) containing 0.05% Tween 20 three times and incubated together with 200 μl of 10% bovine serum albumin (BSA) in phosphate buffer for 30 minutes. After washing with PBST, measurement was carried out. The measurement was carried out by diluting patient's serum 200 or 500 fold with 1% BSA in triplicate. The bo and antibody was allowed to react with goat horseradish peroxidase-conjugated anti-human IgG (American Qualex, diluted 2,000 fold with 1% BSA) at room temperature for 30 minutes. After washed with PBST, the plate was incubated together with 100 μl of 1-Step Slow TMB-ELISA (PIERCE) for 30 minutes. The reaction was stopped by adding 100 μl of 1 M $H_2SO_4$ and absorbance at 450 nm was measured.

Figure 2:
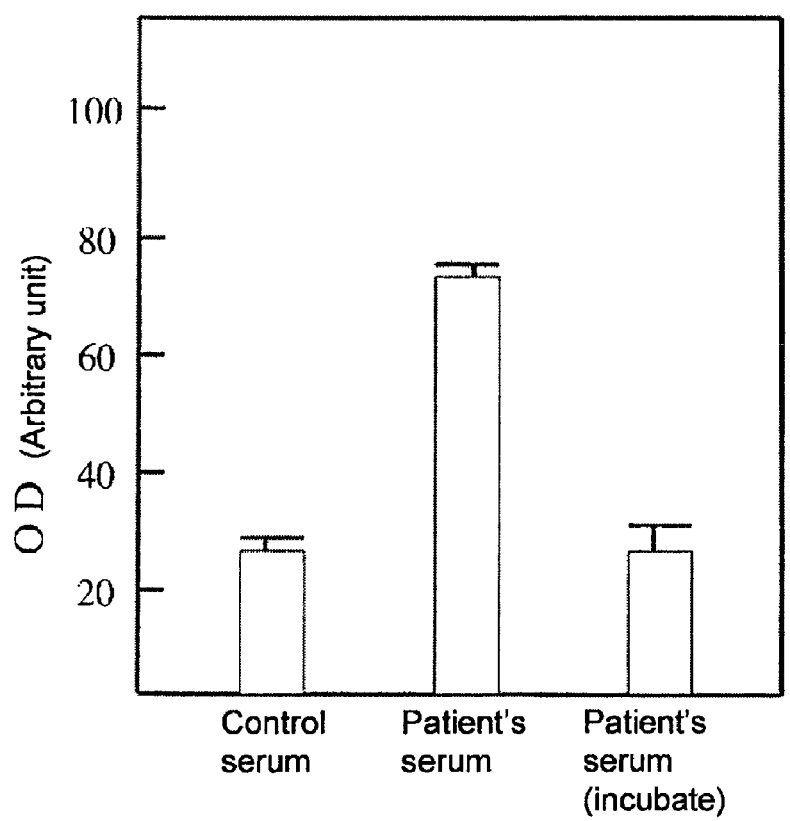
FIG. 2 shows the measurement results of Reference Example 2.

Compared with normal serum (500-fold dilution), patient's serum (500-fold dilution) exhibited a stronger signal. This signal was abolished when patient's serum (500-fold dilution, 1 ml) was previously incubated with the recombinant AMY-2A fragment, AMY-2A/299-512 (1 μg), at 4° C. overnight. The results of the measurement carried out in triplicate are shown in FIG. 2.

Example 1

Figure 3:
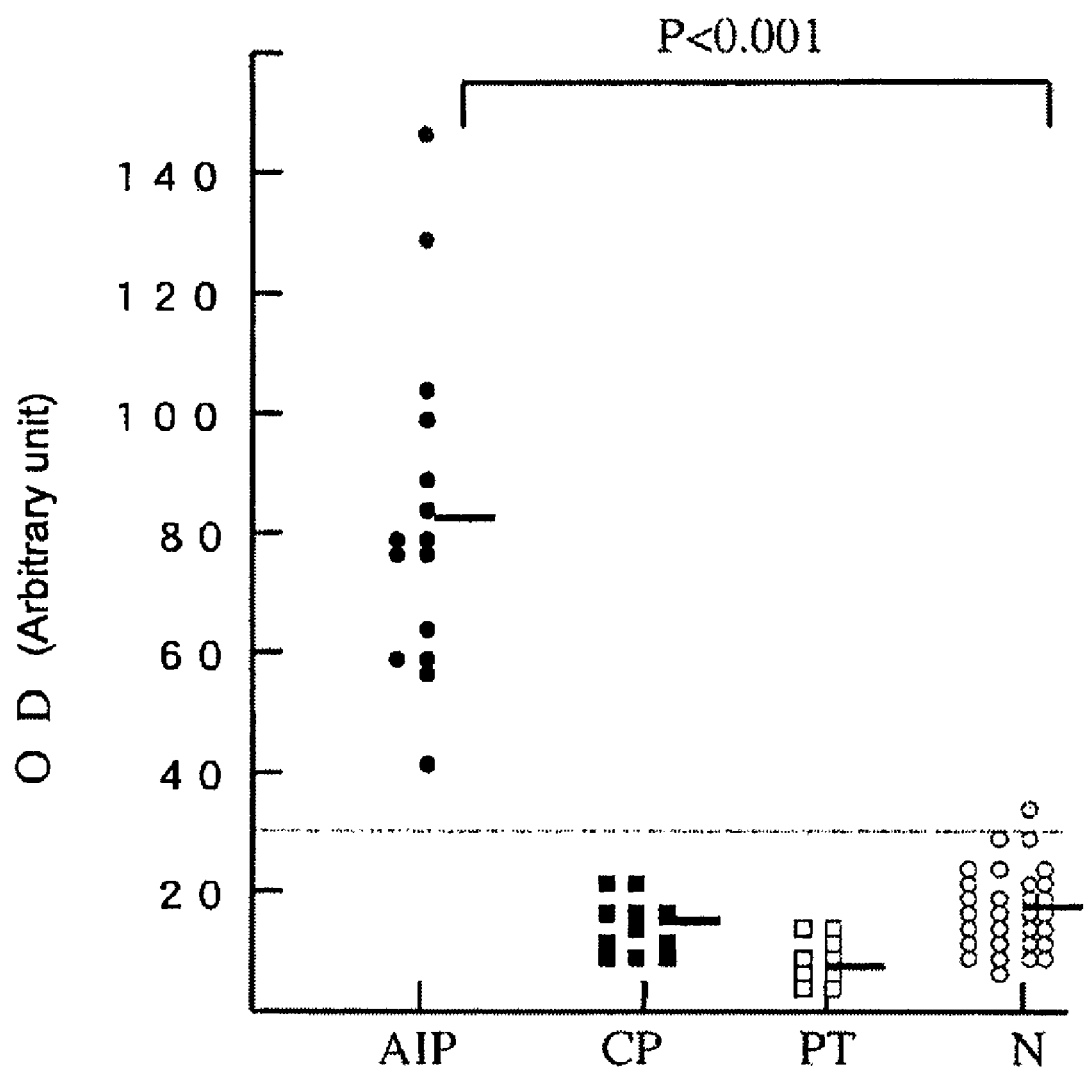
FIG. 3 shows the measurement results of the abundance ratios of the autoantibody against human AMY-2A in patients with various pancreatic diseases, obtained in Example 1. AIP: autoimmune pancreatitis, CP: chronic alcoholic pancreatitis, PT: pancreatic tumors, N: healthy normal subject.

The Abundance Ratio of the Autoantibody Against Human AMY-2A in a Patent with a Pancreatic Disease Using the ELISA in the Reference Example 1, the abundance ratios of the autoantibody against human AMY-2A in patients with various pancreatic diseases were measured (FIG. 3). When a range within ±2SD of values of the healthy normal subjects (n=27) were considered as a normal range, all of the IgG of the AIP patients (n=15) were positive against AMY-2A/299-512. Yet, the sera from the patients with chronic alcoholic pancreatitis (n=13) or patients with pancreatic tumors (pancreatic cancer, n=1; IPMT, n=8) were negative against this antigen.

Figure 4:
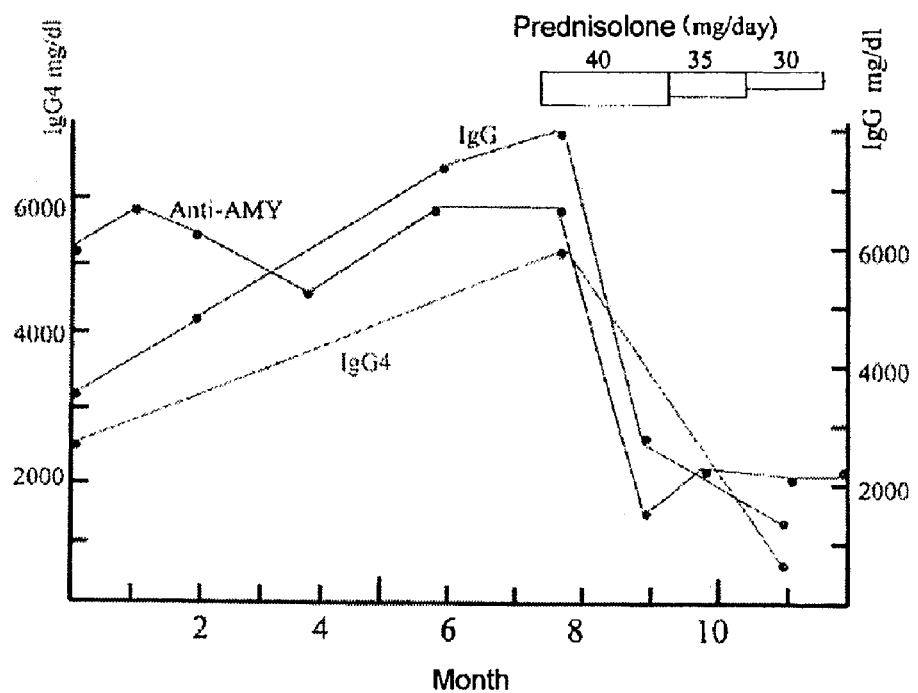
FIG. 4 shows a relationship between treatment progress of the AIP patient and anti-AMY-2 antibody titer, obtained in Example 1.
Figure 5:
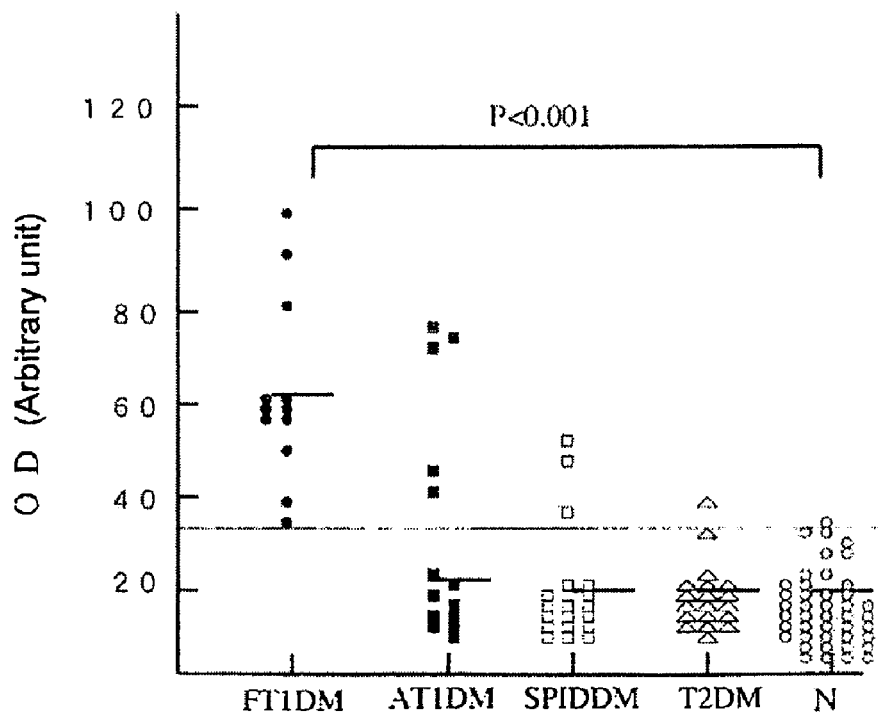
FIG. 5 shows the measurement results of the abundance ratios of the autoantibody against human AMY-2A in patients with various diabetic diseases, obtained in Example 2. FT1DM: fulminant type 1, AT1DM: acute type 1, SPIDDM: slow progressive type 1, T2DM: type 2, N: healthy normal subject.

Further using the ELISA described above, a relationship between treatment progress of the AIP patient and the level of the anti-AMY-2 antibody titer was investigated (FIG. 4). As a result, the level of the anti-AMY-2A antibody titer is decreased by steroid therapy and reflected the disease state better than a concentration of IgG4 in the blood, which has been conventionally said to be useful.

From the above results, it was demonstrated that the present method for examination is a very useful method for the definitive diagnosis and follow up of AIP.

Example 2

The Abundance Ratio of the Autoantibody Against Human AMY-2A in a DM Patient

Using the ELISA in the Reference Example 2, the abundance ratios of the autoantibody against human AMY-2A in patients with various types of DM (fulminant type 1 DM (n=13), acute type 1 DM (n=22), slow progressive type 1 DM (n=19), type 2 DM (n=19)) and healthy normal subjects (n=43) were measured (FIG. 45). All fulminant type 1 DM patients were positive for the autoantibody (p<0.001 vs. normal control). In the patients with acute type 1 DM, slow progress type 1 DM or type 2 DM, the autoantibody was less frequently detected (22%, 15%, and 5%, respectively). Only 2% of the healthy normal subjects showed positive.

Also, when close relatives of the patient who developed FT1DM were subjected to measurement, four out of 16 subjects of the first degree relatives of the patient who developed FT1DM (25%) were found to be positive for the present antibody.

From the results above, by the present measurement, the anti-AMY-2A antibody was proven to be an antibody specific to FT1 DM and the present method for examination was shown to be useful in diagnosis of FT1DM. In addition, a positive individual is present among the first degree relatives at a high frequency, and thus the method was shown to be useful in prediction of developing the disease.

INDUSTRIAL APPLICABILITY

A method for examination of autoimmune pancreatitis (AIP) and fulminant type 1 diabetes mellitus (FT1DM) and reagent therefor are provided.

What is claimed is:

1. A method for examination of a marker of autoimmune pancreatitis in a patient suspected of having autoimmune pancreatitis, said method comprising:
testing a level of an antibody which immunologically reacts with amylase α2-A in a blood sample from the patient,
comparing the level of the antibody in the patient with the level in normal subjects,
determining if the level of the antibody is increased in the patient compared with the level of normal subjects,
wherein the increase in the level of the antibody in the patient compared with normal subjects is a positive marker for autoimmune pancreatitis, thereby indicating autoimmune pancreatitis in the patient.

2. The method for examination according to claim 1, wherein said antibody is detected by an antigen which immunologically reacts with said antibody.

3. The method for examination according to claim 2, wherein said antigen is a partial fragment comprising the amino acid sequence of amino acid numbers 299 to 511 of human amylase α2-A (SEQ ID NO: 1).

4. The method of claim 1, wherein the increase in the level of the antibody is two or more standard deviations higher than normal subjects.

5. A method for examination of a marker of fulminant type 1 diabetes in a patient suspected of having fulminant type I diabetes, said method comprising:
testing a level of an antibody which immunologically reacts with amylase α2-A in a blood sample from the patient,
comparing the level of the antibody in the patient with the level in normal subjects,
determining if the level of the antibody in the patient is increased compared with the level of normal subjects,
wherein the increase in the level of the antibody in the patient compared with normal subjects is a positive marker for fulminant type 1 diabetes, thereby indicating fulminant type I diabetes in the patient.

6. The method for examination according to claim 5, wherein said antibody is detected by an antigen which immunologically reacts with said antibody.

7. The method for examination according to claim 6, wherein said antigen is a partial fragment comprising the amino acid sequence of amino acid numbers 299 to 511 of human amylase α2-A (SEQ ID NO: 1).

8. The method of claim 5, wherein the increase in the level of the antibody is two or more standard deviations higher than normal subjects.

9. A method for determining a risk of developing fulminant type 1 diabetes (FT1DM) in a patient, said method comprising:
detecting a level of an antibody which immunologically reacts with amylase α2-A in a blood sample from the patient having possibility of developing FT1DM,
comparing the level of the antibody in the patient with the level in normal subjects,
determining if the level of the antibody is increased in the patient compared with the level of normal subjects,
wherein the increase in the level of the antibody in the patient compared with normal subjects is a positive marker for thereby determining the increased risk of developing fulminant type 1 diabetes in the patient.

10. The method for examination according to claim 9, wherein said antibody is detected by an antigen which immunologically reacts with said antibody.

11. The method for examination according to claim 10, wherein said antigen is a partial fragment comprising the amino acid sequence of amino acid numbers 299 to 511 of human amylase α2-A (SEQ ID NO: 1).

12. The method of claim 9, wherein the increase in the level of the antibody is two or more standard deviations higher than normal subjects.

\* \* \* \* \*

UNITED STATES PATENT AND TRADEMARK OFFICE
CERTIFICATE OF CORRECTION

PATENT NO. : 8,278,119 B2
APPLICATION NO. : 12/598416
DATED : October 2, 2012
INVENTOR(S) : Kobayashi et al.

It is certified that error appears in the above-identified patent and that said Letters Patent is hereby corrected as shown below:

In the Specifications:

In column 5 at line 37, Change "thiogalactsides" to --thiogalactoside--.

In column 6 at line 33, Change "bo and" to --bound--.

In column 6 at line 60, Change "against" to --against the recombinant AMY-2A fragment,--.

In column 7 at line 14, Change "in the" to --in--.

Signed and Sealed this
Second Day of July, 2013

Teresa Stanek Rea
*Acting Director of the United States Patent and Trademark Office*